United States Patent
Simundic et al.

(10) Patent No.: US 10,729,840 B2
(45) Date of Patent: Aug. 4, 2020

(54) ASSEMBLY COMPRISING A SUCTION LINE, A PRESSURE LINE AND A PUMP

(71) Applicant: Xenios AG, Heilbronn (DE)

(72) Inventors: Ivo Simundic, Wendlingen (DE); Georg Matheis, Heilbronn (DE); Petr Ostadal, Prague (CZ)

(73) Assignee: XENIOS AG, Heilbronn (DE)

( * ) Notice: Subject to any disclaimer, the term of this patent is extended or adjusted under 35 U.S.C. 154(b) by 0 days.

(21) Appl. No.: 15/660,080

(22) Filed: Jul. 26, 2017

(65) Prior Publication Data

US 2017/0319774 A1    Nov. 9, 2017

Related U.S. Application Data

(63) Continuation of application No. PCT/DE2016/000025, filed on Jan. 26, 2016.

(30) Foreign Application Priority Data

Jan. 26, 2015   (DE) ..................... 10 2015 000 771

(51) Int. Cl.
   *A61M 37/00*   (2006.01)
   *A61M 1/36*    (2006.01)
   *A61M 1/10*    (2006.01)

(52) U.S. Cl.
   CPC ........ *A61M 1/3659* (2014.02); *A61M 1/1008* (2014.02); *A61M 1/3666* (2013.01); *A61M 1/3667* (2014.02); *A61M 1/10* (2013.01); *A61M 1/1001* (2014.02); *A61M 1/1005* (2014.02); *A61M 1/1086* (2013.01); *A61M 2230/04* (2013.01)

(58) Field of Classification Search
   CPC .............. A61M 1/3659; A61M 1/1008; A61M 1/3667; A61M 1/3666; A61M 1/1001; A61M 1/1005; A61M 1/10; A61M 1/1086; A61M 2230/04
   USPC ....................................... 604/4.01
   See application file for complete search history.

(56) References Cited

U.S. PATENT DOCUMENTS 5,011,469 A * 4/1991 Buckberg ............ A61M 1/3621
                                                 604/508
5,433,700 A * 7/1995 Peters ............... A61M 25/0026
                                                 604/113

(Continued)

FOREIGN PATENT DOCUMENTS

DE       89 90 089 U1    8/1991
DE       695 24 217 T2   8/2002

(Continued)

OTHER PUBLICATIONS

International Search Report of PCT/DE2016/000025, dated Aug. 29, 2016.

*Primary Examiner* — Andrew J Mensh
(74) *Attorney, Agent, or Firm* — Collard & Roe, P.C.

(57) ABSTRACT

An assembly for an extracorporeal life support system with a suction line that features a venous cannula and a pressure line that features an arterial cannula furthermore includes a pump that is arranged between the suction line and the pressure line. This assembly has a discharge line with a discharge cannula, wherein the discharge cannula is longer than the arterial cannula, and wherein the discharge line is connected to the suction line or the pressure line.

4 Claims, 4 Drawing Sheets

(56) References Cited

U.S. PATENT DOCUMENTS

| | | |
|---|---|---|
| 5,478,309 A | 12/1995 | Sweezer et al. |
| 2002/0087107 A1 | 7/2002 | Roberts et al. |
| 2008/0249456 A1* | 10/2008 | Inamori .............. A61M 1/1086 604/6.1 |
| 2010/0187333 A1 | 7/2010 | Escoto, Jr. et al. |
| 2011/0112353 A1* | 5/2011 | Farnan .................... A61M 1/10 600/16 |
| 2011/0160517 A1* | 6/2011 | Smith ................. A61M 1/3621 600/16 |
| 2013/0320110 A1 | 12/2013 | Brose et al. |
| 2015/0030502 A1 | 1/2015 | Gorhan et al. |

FOREIGN PATENT DOCUMENTS

| | | |
|---|---|---|
| EP | 2 832 383 A1 | 2/2015 |
| JP | 2008-264512 A | 11/2008 |
| JP | 4-501220 B2 | 7/2010 |

\* cited by examiner

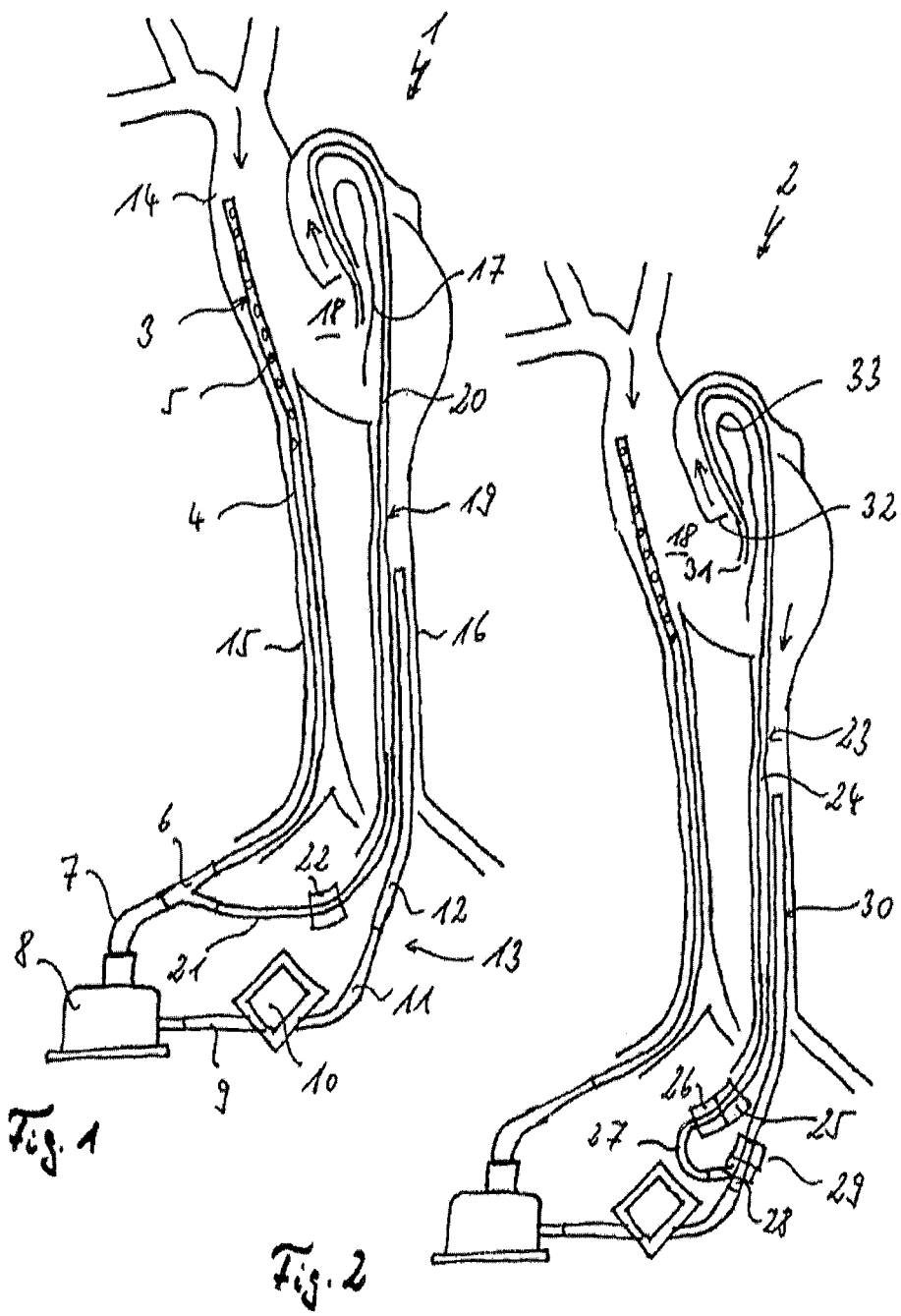

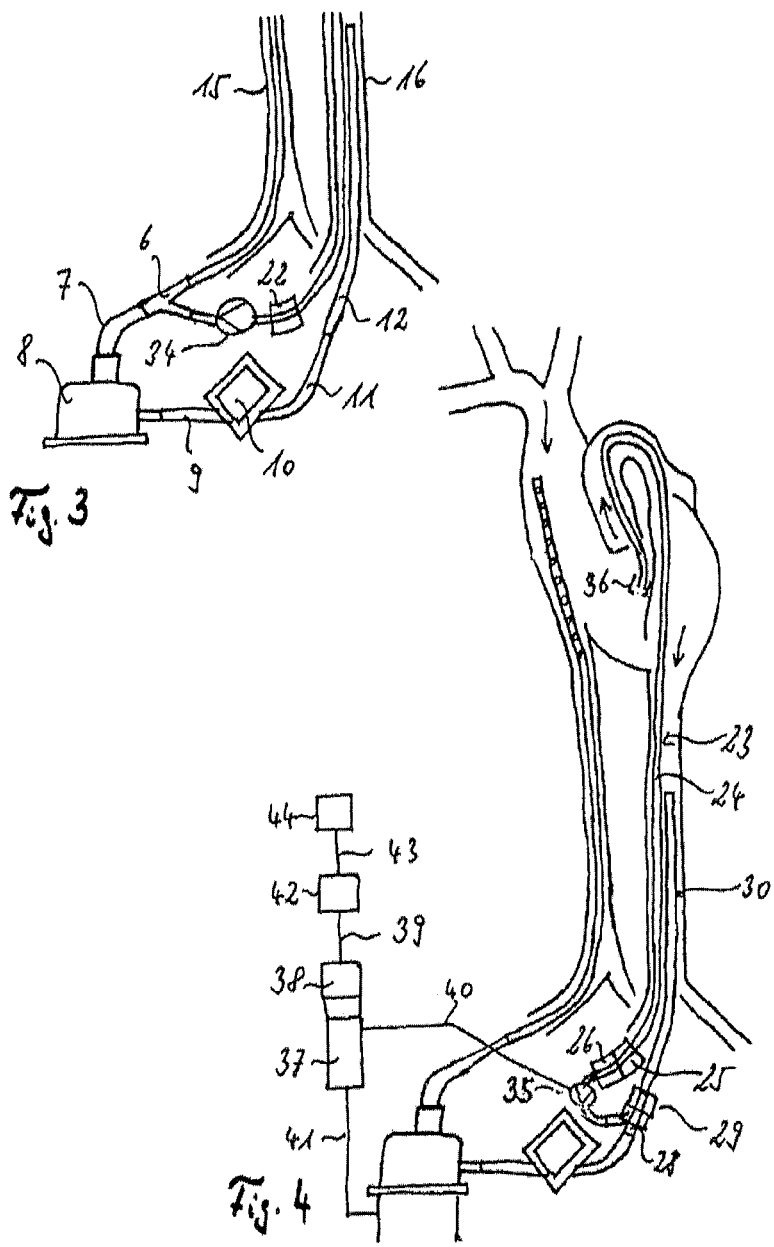

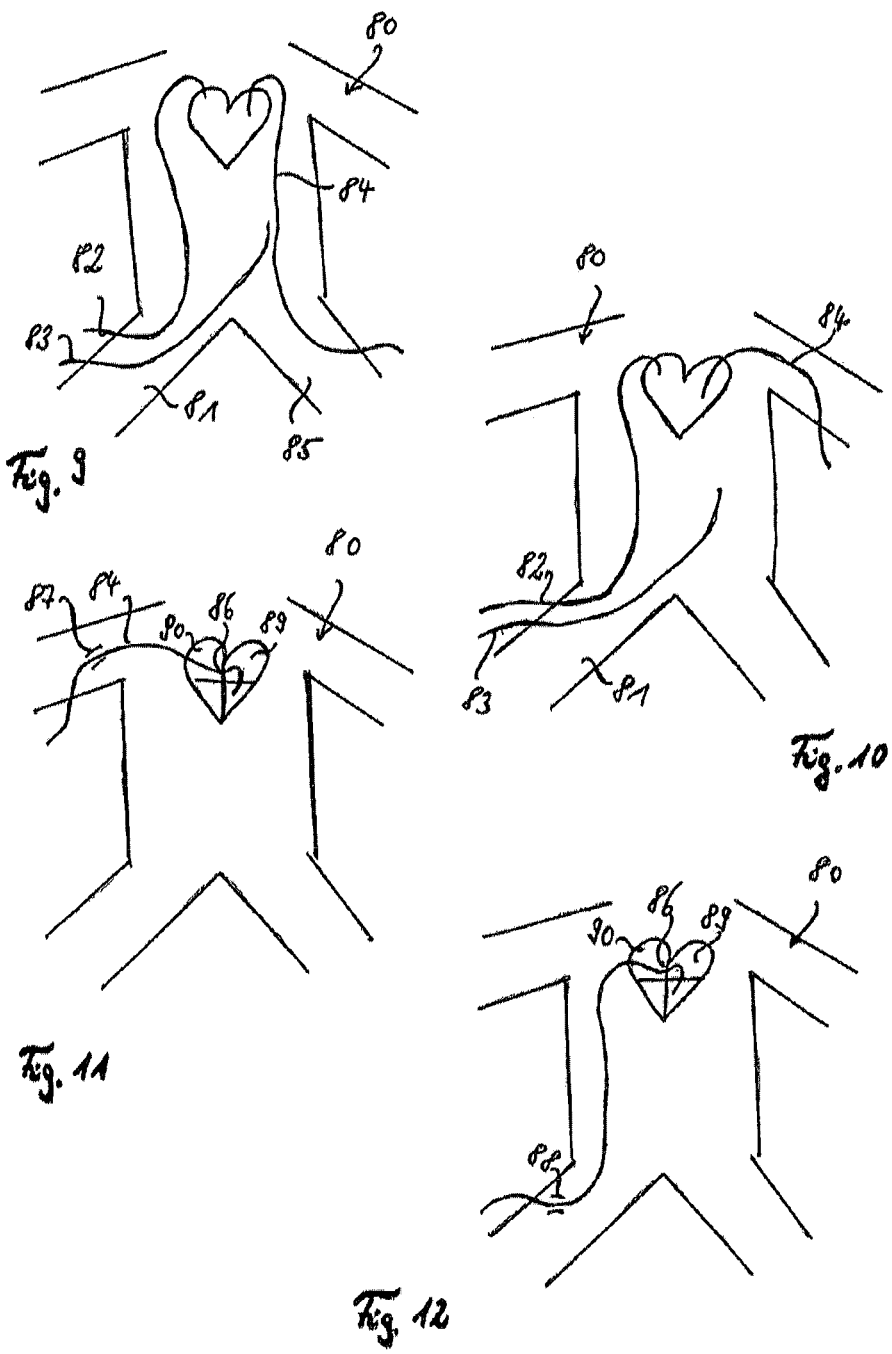

ASSEMBLY COMPRISING A SUCTION LINE, A PRESSURE LINE AND A PUMP

CROSS REFERENCE TO RELATED APPLICATIONS

Applicant claims priority and this application is a continuation under 35 U.S.C. § 120 of International Application No. PCT/DE2016/000025 filed Jan. 26, 2016, which claims priority under 35 U.S.C. § 119 of German Application No. 10 2015 000 771.8 filed on Jan. 26, 2015. The International Application under PCT article 21(2) was not published in English. The disclosures of the aforesaid International Application and German application are incorporated herein by reference.

BACKGROUND OF THE INVENTION

1. Field of the Invention

The invention pertains to an assembly with a suction line that features a venous cannula, a pressure line that features an arterial cannula and a pump that is arranged between the suction line and the pressure line.

Such assemblies are used for extracorporeal membrane oxygenation or for extracorporeal lung assist. In extracorporeal membrane oxygenation, cannulas are inserted into two large blood vessels. The ECMO-device pumps blood through a membrane oxygenator that replaces the gas exchange in the lung. The thusly processed blood is then fed to the patient. The invention particularly pertains to a device for veno-arterial ECMO (VA-ECMO). In VA-ECMO, blood is removed from large veins such as, in particular, the vena femoralis and conveyed past the heart into an artery (arteria femoralis) such that a parallel circulatory system is formed. Since the heart is thereby relieved, this method is used on patients with inferior pumping function of the heart (e.g. heart failure, cardiogenic shock). Systems of this type are also referred to as extracorporeal life support systems (ECLS).

2. Description of the Related Art

DE 695 24 217 T2 describes a cardioplegia catheter that is inserted via the clavicle and serves for administering a mixture of blood and cardioplegic solution or a pure crystalloid solution. This catheter features an arterial cannula, to which a short discharge cannula with a balloon is connected.

DE 89 90 089 U1 describes an elaborate assembly with multiple pumps, discharge lines and reservoirs that are difficult to operate in practical applications.

US 2002/0087107 A1 and US 2011/0112353 describe systems that are used as cardiac assist systems during open-heart surgery or subcutaneously. However, the design and the assembly of the catheters do not make it possible to supply the heart with an arterial cannula and to simultaneously relieve the heart with a ventilation cannula on the side of the same ventricle.

SUMMARY OF THE INVENTION

The invention is based on the objective of enhancing such an ECLS system.

This is achieved in that the inventive assembly features a discharge line with a discharge cannula, wherein the discharge cannula is longer than the arterial cannula and the discharge line is connected to the suction line or the pressure line. The discharge cannula is particularly realized in the form of a ventilation cannula that is longer than the arterial cannula and the discharge line is connected directly to the suction line or directly to the pressure line, wherein only a single pump and no reservoir is arranged between the suction line and the pressure line.

In contrast to DE 695 24 217 T2, the inventive discharge cannula preferably is a continuous one-piece cannula. The inventive cannula has no balloon on the end that can be inserted into the heart. Contrary to a balloon catheter, the proximal end is according to the invention realized with a constant diameter such that blood can flow adjacent to the ventilation cannula. Consequently, the inventive ventilation cannula also has no further access to a balloon. In this way, the available diameter on the cannula can be used in its entirety for a flow of blood.

The inventive cannula therefore only has one lumen for a flow of blood in the direction toward the heart and one lumen for a flow of blood in the direction away from the heart. Additional lumens or channels are not required and even disadvantageous.

In DE 695 24 217 T2, a sensor is furthermore provided on the flexible proximal end. This sensor also leads to an elaborate design and requires a line in the cannula in order to transmit the measured values. The inventive assembly consists exclusively of blood lines and neither requires electric lines for transmitting sensor signals nor pneumatic lines for operating a balloon.

DE 89 90 089 U1 describes a bypass system analogous to DE 695 24 217 T2, in which the heart is initially pumped bloodless. Consequently, a reservoir in the form of a cardiotomy reservoir is required in such systems. The inventive assembly, in contrast, is intended for therapy and requires no such cardiotomy reservoir.

The discharge cannula makes it possible to return a flow of blood discharged from the heart in order to relieve the heart at the moment of the inflow through the arterial cannula. The discharge cannula can also be referred to as a relief cannula, and the discharge line can also be referred to as a relief line. In this case, the arterial cannula preferably already ends in the artery in front of the heart whereas the discharge cannula is pushed far into the heart. The discharge cannula therefore is at least 20% longer than the arterial cannula in practical applications.

The assembly can be used as a pure heart assist system. However, it can advantageously also be used as a lung assist system, in which an oxygenator is arranged between the suction line and the pressure line.

The discharge line is particularly advantageous if the pump generates a pulsating flow. In this case, a discharge through the discharge line can be realized at the moment of the pressure increase at the pump and therefore in the artery and in the heart. The assembly is therefore primarily suitable for pulsatile pumps. An oxygenator is particularly required as part of a pulsatile operation for circulatory assist purposes because the blood is partially conveyed past the lungs.

In order to adjust the discharge intensity independently of the diameter of the discharge line, it is proposed that the discharge line features a flow restrictor. This flow restrictor can reduce the volume flow conveyed through the discharge line in order to adjust a more or less intense discharge at the heart.

It is particularly advantageous if the control makes it possible to automatically adjust the flow restrictor in dependence on the pulsating flow. This makes it possible to cause a discharge during a pressure increase of the pulsatile pump and to control or adjust the moment of the discharge in dependence on the moment of the pressure increase and, in particular, in dependence on the pumping rhythm of the heart.

In order to introduce the return flow of the discharge line into the suction line or into the pressure line with the least turbulences possible, it is proposed to arrange a Y-adapter between the discharge line and the suction line or the pressure line. This Y-adapter is respectively arranged in such a way that the incoming flow of blood is combined with the respective other flow of blood at an obtuse angle.

The connection of the discharge line to the pressure or suction line by means of a Y-adapter alone ensures that the discharge cannula causes the heart to be relieved by discharging blood. If the discharge line is connected to the pressure line, however, it is frequently advantageous if the discharge line features a check valve. This prevents the pump from pumping blood into the discharge line.

According to a preferred embodiment, it is proposed that the discharge line is connected to the pressure line by means of a Venturi nozzle. Consequently, a vacuum is generated in the region of the junction of the discharge line by means of a Venturi or injector nozzle and ensures that blood is removed from the discharge line by suction.

A cannula with a length between 80 cm and 100 cm, preferably between 85 cm and 95 cm, is particularly suitable for the inventive assembly. A size between 7 Fr and 9 Fr or an outside diameter between 2 mm and 3 mm is advantageously used.

The cannula advantageously features a flow restrictor. In this context, the cannula may also be connected to a flow restrictor by means of a corresponding line. It should be possible to automatically adjust and thereby adapt such a flow restrictor to the pulse of the pump and preferably also the pulse of the heart.

BRIEF DESCRIPTION OF THE DRAWINGS

Several exemplary embodiments of inventive assemblies are illustrated in the drawings and described in greater detail below. In these drawings, FIG. 1 shows an extracorporeal life support system, in which the discharge line leads into the suction line, FIG. 2 shows an extracorporeal life support system, in which the discharge line leads into the pressure line, FIG. 3 shows a detail of the extracorporeal life support system according to FIG. 1 with a second pump, FIG. 4 shows an extracorporeal life support system according to FIG. 2 with a second pump.

DETAILED DESCRIPTION OF PREFERRED EMBODIMENTS

Figure 5:
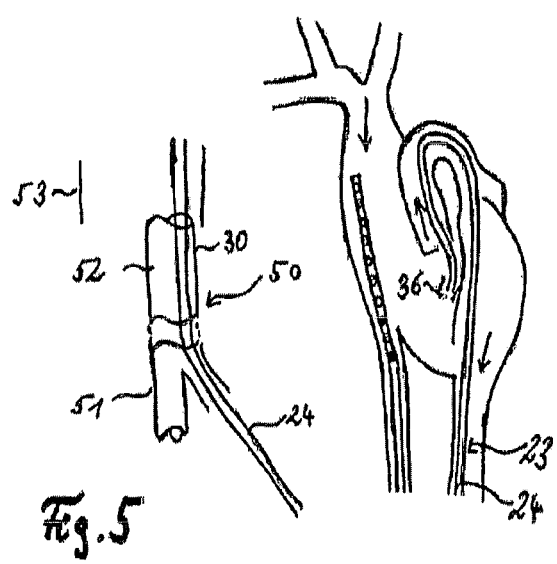
FIG. 5 shows an assembly according to FIG. 4 with a Y-adapter.

According to the first exemplary embodiment illustrated in FIG. 1, the extracorporeal life support system 1, 2 has a suction line 3 that features a venous cannula 4 with bores 5, a Y-adapter 6 and a feed line 7 leading to a pump 8. Only the pump head of the pump 8 is illustrated in this figure. The pump 8 is connected to an oxygenator 10 by means of a connecting line 9, wherein the oxygenator is connected to an arterial cannula 12 by means of a delivery line 11. The delivery line 11 and the arterial cannula 12 form a pressure line 13.

While the assembly is in use, blood can therefore be drawn from the heart 14 to the pump 8 through the vena femoralis 15 by means of the venous cannula 4 of the suction line 3 in order to be subsequently conveyed into the left ventricle via the oxygenator 10 and the arterial cannula 12, namely through the arteria femoralis 16 and the aorta via the aortic arch. In this way, the heart 14 is bypassed and therefore relieved.

If a pulsatile pump 8 is used, an overpressure is generated in the arteria femoralis 16 at the moment of maximum pressure and presses against the wall 17 of the heart. It is therefore advantageous to reduce the pressure in the region 18 behind the wall 17 of the heart at this moment by removing blood by suction. This is achieved with a discharge line 19 that comprises a discharge cannula 20 and a discharge line 21. This discharge cannula 20 makes it possible to convey blood from the heart 14 through the arteria femoralis 16 and to the Y-adapter 6, from where the blood reaches the pump 8 through the feed line 7. Consequently, the pump 8 not only draws blood from the venous cannula 4, but also from the discharge cannula 20. Even without a suction effect, the discharge cannula already serves for relieving an overpressure and therefore the heart.

The volume flow being returned through the discharge line 19 can be varied by means of the flow restrictor 22. The flow restrictor 22 may be provided optionally and is connected to a (not-shown) control that controls or adjusts the flow through the discharge line 19 and the pump 8. In this way, the discharge can be arbitrarily varied and, in particular, controlled in dependence on the pumping capacity during the operation of the pump while the assembly is in use. According to a preferred embodiment, it is proposed that the pumping capacity and therefore also indirectly the flow restrictor are controlled in dependence on the heart rhythm, i.e. the EKG-signal.

The alternative embodiment of the assembly 2 illustrated in FIG. 2 is essentially designed and used in the same way as the assembly illustrated in FIG. 1. However, the discharge line 23 features a discharge cannula 24 that is connected to a Y-adapter 28 by means of a flow restrictor 25, a check valve 26 and a line 27. In the present exemplary embodiment, the Y-adapter 28 is realized in the form of a Venturi nozzle 29. This allows a simplified design without a check valve 26 and without a flow restrictor 25 because the Venturi nozzle also causes a stronger vacuum and therefore greater suction on the discharge line 23 at the moment of an increased flow through the pressure line 30.

As in the exemplary embodiment illustrated in FIG. 1, the cannula inlet 31 of the discharge line 23 of the discharge cannula 24 lies in the region 18 behind the aortic valve 32 and the aortic arch 33 while the cannula is in use.

FIG. 3 shows an embodiment that is essentially designed in the same way as the embodiment illustrated in FIG. 1. However, a pump 34, which is preferably realized in the form of a suction pump, is provided between the discharge line 19 and the Y-adapter 6 in this exemplary embodiment. This pump 34 in the form of a suction pump can be activated independently of the pump 8. It may consist of a non-pulsatile or pulsatile pump and be operated synchronously with the pump 8 or phase-shifted relative to the pump 8. In this case, the pump 8 fulfills the function of the main pump and the pump 34 fulfills the function of an assist pump.

An additional pump 35 is also provided between the discharge line 23 and the Y-adapter 28 in FIG. 4, which shows an exemplary embodiment according to FIG. 2. An EKG-triggered pulsatile control with or without additional suction pump 35 is also advantageous in this exemplary embodiment.

A pump control 37 is provided for this purpose and connected to the pump 8 and—if applicable—to an additional pump 35 (see FIG. 4) or an additional pump 34 (see FIG. 3). A computer 38 converts a control signal 39 into a pump driving signal 40, 41. This pump driving signal is used by the pump control 37 for realizing a pumping capacity of the pump 8, which increases and decreases in waves, and can furthermore ensure a synchronous or time-shifted and pulsatile or not-pulsatile pumping capacity of the pumps 34 or 35, which may also be dependent on or independent of the pumping capacity of the main pump 8. The control signal 39 is generated by an EKG 42 that is connected to the patient 44 by means of a cable 43.

During the operation of the ECLS system, an EKG-signal of the patient 44 is acquired with the EKG 42 via the cable 43 in order to generate the control signal 39. This control signal 39 is converted into the pump signal 40, 41 by means of the computer 38 and serves for controlling the pumps 8, 34 and 35 by means of the pump control 37 or for supplying said the pumps with power. This makes it possible to realize an SW-trigger for operating the pumps in accordance with a special algorithm in order to deliver pulses during the systole and/or the diastole. A device and a method of this type are described in EP 2 832 383 and the corresponding description forms part of this application.

In the exemplary embodiment illustrated in FIG. 4, a spacer 36 is provided on the end 31 of the discharge cannula 24. This spacer 36 prevents the cannula inlet 31 from being sucked against the wall 17 of the heart. This can be realized with a cage-like design or a spiral-shaped design of the end 31, which is also referred to as pigtail.

In all exemplary embodiments, the venous cannula 4 has a length of 55 cm and a preferred size between 19 Fr and 25 Fr. The cannula has a size, for example, between 21 and 25 Fr. The arterial cannula preferably has a length of 38 cm and a size between 13 Fr and 17 Fr, preferably between 15 and 16 Fr. The discharge cannula is smaller than the venous cannula and smaller than the arterial cannula. It has a size between 7 Fr and 9 Fr and a length of 90 cm.

FIG. 5 shows a slightly enlarged illustration of a Y-adapter 50, in which the discharge cannula 24 can be inserted into the pressure line 30 in the form of a ventilation cannula such that it is not required to route two cannulas adjacent, to one another in the vessel. The ventilation cannula is realized with a size of 6, 7 or 8 Fr and the adjacent branch 51 has a size of ⅜". The cannula shaft 52 of the perfusion cannula routed in the indicated aorta 53 has a size of 13, 16 or 18 Fr and the ventilation cannula 24 is inserted therein in a floating fashion.

Figure 6:
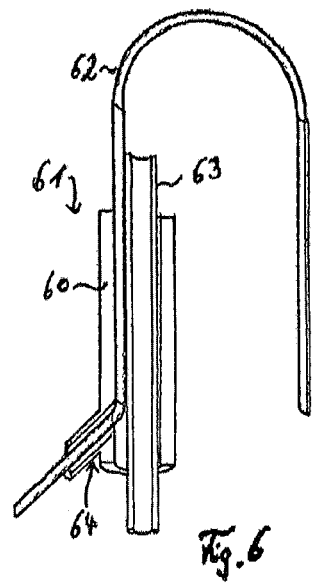
FIG. 6 shows the routing of a pressure line and a smaller discharge line in a cannula.

In the exemplary embodiment illustrated in FIG. 6, the ventilation cannula 62 and the pressure line 63 are routed within the wall 60 of a catheter 61. For this purpose, the ventilation cannula 62 is inserted into the Y-inlet 64 and then routed adjacent to the pressure line 63. According to a not-shown embodiment, the ventilation cannula 62 is inserted into the pressure line 63 and then routed within the pressure line 63.

Figure 7:
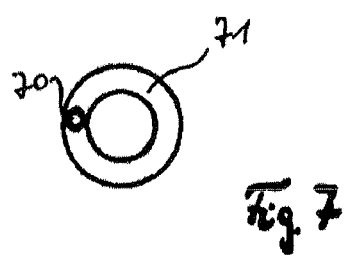
FIG. 7 shows a cross section through the routing of a discharge line in a cannula.
Figure 8:
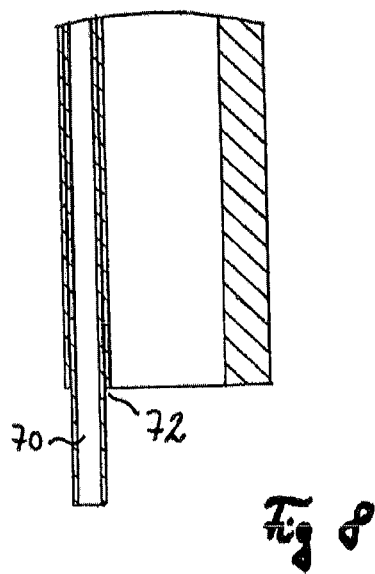
FIG. 8 shows a longitudinal section through the cannula routing illustrated in FIG. 7, FIG. 9 schematically shows bilateral access of the discharge cannula, FIG. 10 schematically shows access of the discharge cannula through a vena *brachialis*, FIG. 11 schematically shows access of the discharge cannula through the superior vena cava and an atrial septum, and FIG. 12 schematically shows access of the discharge cannula through the inferior vena cava and an atrial septum.

FIGS. 7 and 8 show how a ventilation cannula 70 can be routed in an inner cannula lumen 71. In this case, a working channel 72 for the ventilation cannula 70 is provided in the lumen 71. The wall of the cannula may be thickened in the region of the working channel 72 if the wall is not sufficiently thick for arranging a working channel therein.

FIGS. 9-12 show how a discharge or ventilation cannula can be routed in the body 80 of a patient. The lengths and designs of the cannula differ depending on the respective routing.

In the example illustrated in FIG. 9, the suction line 82 is venously inserted and the pressure line 83 is arterially inserted into a leg 81. The discharge line 84 is routed in the other leg 85.

In the example illustrated in FIG. 10, the suction line 82 is venously inserted and the pressure line 83 is arterially inserted into a leg 81. The discharge line 84 is routed in the arteria *brachialis*.

FIGS. 11 and 12 show access through an atrial septum 86. In this case, the ventilation cannula 84 is either routed through the superior vena cava 87 as shown in FIG. 11 or through the inferior vena cava 88 as shown in FIG. 12. The atrial septum 86 lies between the atria 89 and 90.

The embodiments shown relieve the heart, particularly in case of insufficient pumping capacity or output capacity. The myocardium-protective effect of the diastolic augmentation significantly intensifies, in particular, during a pulsatile EKG-triggered operation of one or both pumps (lower afterload, increase of the left ventricular output capacity, reduction of the left ventricular residual volume) due to the reduced ventricle volume. This additionally relieves the left ventricle and lowers the wall tension, especially during the diastole, such that the coronary flow can be positively influenced.

What is claimed is:

1. An assembly for an extracorporeal life support system with
   a suction line that features a venous cannula,
   a pressure line that features an arterial cannula,
   a pump that is arranged between the suction line and the pressure line, the pump generating a pulsating flow,
   a relief line with a relief cannula, a diameter, and a flow restrictor, wherein the flow restrictor is disposed in the relief line, and wherein the flow restrictor is automatically adjustable in dependence on the pulsating flow in order to adjust relief intensity independently of the diameter of the relief line and reduce volume flow conveyed through the relief line in dependence on pumping rhythm of the heart, and
   an oxygenator arranged between the suction line and the pressure line,
   wherein the pump is configured to cause a suction in the suction line and in the relief line and to influence a volume of blood that is pumped,
   wherein the relief cannula is realized in the form of a ventilation cannula,
   wherein the relief line is connected directly to the pressure line,
   wherein only a single pump and no reservoir is arranged between the suction line and the pressure line, and
   wherein the relief cannula is longer than the arterial cannula.

2. The assembly according to claim 1, wherein a Y-adapter is arranged between the relief line and the pressure line.

3. The assembly according to claim 1, wherein the relief line features a check valve.

4. The assembly according to claim 1, wherein the relief line is connected to the pressure line via a Venturi nozzle.

* * * * *